(12) United States Patent
Shibata et al.

(10) Patent No.: US 6,726,620 B2
(45) Date of Patent: Apr. 27, 2004

(54) ENDOSCOPIC IMAGE FILING SYSTEM FOR MANAGING CLEANING INFORMATION OF ENDOSCOPE WITH IMAGE INFORMATION

(75) Inventors: Hiroyuki Shibata, Yokohama (JP); Makoto Watai, Hachioji (JP); Nobuyasu Ito, Hachioji (JP)

(73) Assignee: Olympus Corporation, Tokyo (JP)

( * ) Notice: Subject to any disclaimer, the term of this patent is extended or adjusted under 35 U.S.C. 154(b) by 481 days.

(21) Appl. No.: 09/852,413

(22) Filed: May 10, 2001

(65) Prior Publication Data

US 2001/0041825 A1 Nov. 15, 2001

(30) Foreign Application Priority Data

May 12, 2000 (JP) ......................... 2000-140765
Sep. 8, 2000 (JP) ......................... 2000-273792

(51) Int. Cl.[7] ................................. A61B 1/04
(52) U.S. Cl. .................. 600/118; 600/133; 600/109; 348/65
(58) Field of Search ................. 600/118, 117, 600/133, 109; 348/65, 67, 68, 71, 72, 73, 74, 75

(56) References Cited

U.S. PATENT DOCUMENTS

| | | | | |
|---|---|---|---|---|
| 4,402,311 A | * | 9/1983 | Hattori ................... 600/117 |
| 4,475,541 A | * | 10/1984 | Takamatsu et al. ........ 600/109 |
| 4,503,841 A | * | 3/1985 | Tsukaya et al. .......... 600/118 |
| 4,509,508 A | * | 4/1985 | Tsukaya ................. 600/118 |
| 4,590,924 A | * | 5/1986 | Tanikawa et al. ......... 600/109 |
| 4,862,872 A | | 9/1989 | Yabe et al. |
| 5,111,306 A | | 5/1992 | Kanno et al. |
| 5,164,824 A | * | 11/1992 | Ieoka et al. ............. 348/71 |
| 5,209,220 A | | 5/1993 | Hiyama et al. |
| 5,877,819 A | | 3/1999 | Branson |
| 6,436,032 B1 | * | 8/2002 | Eto et al. ............... 600/117 |

FOREIGN PATENT DOCUMENTS

| | | |
|---|---|---|
| JP | 2000-33072 | 2/2000 |
| JP | 2001-46326 | 2/2001 |
| WO | WO 99/66444 | 12/1999 |

* cited by examiner

Primary Examiner—Henry Bennett
Assistant Examiner—Fadi H. Dahbour
(74) Attorney, Agent, or Firm—Scully, Scott, Murphy & Presser

(57) ABSTRACT

An endoscopic image filing system mainly comprises an endoscope apparatus for performing endoscopical examination by way of an endoscopic image, an image filing apparatus connected with the endoscope apparatus for recording a required endoscopic image, and a cleaning apparatus for sterilizing/cleaning an endoscope used in the endoscope apparatus. The image filing apparatus is provided with a keyboard and a mouse for inputting and setting a variety of data. The cleaning apparatus is provided with a keyboard for inputting data and a printer for printing a sticker or the like which indicates that the endoscope has already been cleaned and is stuck for the endoscope after cleaned, for example. The cleaning apparatus is capable of transmitting cleaning information to the image filing apparatus.

16 Claims, 16 Drawing Sheets

FIG.8

INFORMATION OF EXAMINATION — 61a

| | | |
|---|---|---|
| TYPE OF EXAMINATION — 61aa | EXAMINATION ROOM — 61l | DATE OF EXAMINATION — 61ab, 61ac |
| Bauchpinselung | ROOM5 | 4/3/98 |

EXAMINATION NUMBER: BA9804001

PATIENT INFORMATION
FAMILY NAME: CCCC
GIVEN NAME — 61ae: DDDD

INTRODUCER
FULL NAME
ADDRESS

DATE OF AGREEMENT — 61ah

☐ URGENT

HOSPITALIZED/VISITED
◉ INPATIENT
○ OUTPATIENT

START TIME — 61ad: 09:00
COMPLETION TIME: 09:17

STAFF — 61ag
TEAM OF EXAMINATION: EGD All Stars
PERSON IN CHARGE OF EXAMINATION: Akita
ASSISTANT 1: Althoff
ASSISTANT 2: Aomori
ASSISTANT 3: Chiba
NURSE 1: Fukuoka
NURSE 2: Hirosima
NURSE 3: Ishukawa ENDOSCOPE
SCOPE 1: AB-123    SCOPE NUMBER: 4000004962
SCOPE 2: AB-123    SCOPE NUMBER: 1000001971

SYMPTOMS
MMMMMMMMMM
MMMMMMMMMM
MMMMMM
Indication item1

PRINCIPAL DIAGNOSIS — 61ai
4/14/98
MMMMMMMMMM
MMMMMMMMMM
MMMMMM
4/8/98 Main Diagnosis item3
4/8/98 Main Diagnosis item1

PRETREATMENT
tbs glucagon
100ml topical xylocaing

ADDITIONAL INFORMATION — 61aj
MMMMMMMMMM
MMMMMMMMMM
MMMMMMMMMM
MMMMMMMMMM
MMMMMMMMMM

UNDO — 61c          OK — 61d    CANCEL — 61e

ENDOSCOPE

TYPE OF ENDOSCOPE

| TYPE OF ENDOSCOPE | ENDOSCOPE ID | SORT OF EXAMINATION | INTERNAL SCOPE NUMBER |
|---|---|---|---|
| ▲ | | | |
| GIF TYPE Q140 | 4545 | UPPER DIGESTIVE TRACT | OLM-001D |
| GIF TYPE Q240 | 3030 | UPPER DIGESTIVE TRACT | OLM-001C |
| GIF TYPE SP240 | 2020 | UPPER DIGESTIVE TRACT | OLM-001B |
| GIF TYPE XP160 | 1234 | UPPER DIGESTIVE TRACT | |
| GIF TYPE XQ240 | 1010 | UPPER DIGESTIVE TRACT | OLM-001A |

| ADD | EDIT | DELETE |   | OK | CANCEL |

REGISTRATION OF ENDOSCOPE

MODEL NAME OF ENDOSCOPE

ENDOSCOPE ID

TYPE OF EXAMINATION

| UNDO |   | OK | CANCEL |

HISTORY OF SCOPE

| DATE | START TIME | COMPLETION TIME | TYPE OF SCOPE | NUMBER FOR MANAGEMENT | SERIAL No. OF CLEANING APPARATUS | PROGRAM | EXPLANATION |
|---|---|---|---|---|---|---|---|
| 06.12.1997 | 14:56:33 | 15:30:36 | GIF-Q140 | 12 | 005979 | ECO | BY ETD |
| 06.12.1997 | 15:50:31 | 16:28:20 | BF-30 | 25 | 005979 | ECO | BY ETD |
| 07.12.1997 | 13:40:11 | 14:27:11 | GIF-Q130 | 89 | N/A | N/A | MANUAL CLEANING |

[ ALL ]

DETAILS

PROTOCOL P2>0083<

USER:Nurse Brenda
SCOPE1:12 GIF-Q140
06.12.97 SERIAL NUMBER005979
14:56:33 ECO
14:56:33 DITS
15:00:14 CLEANING
15:08:51 STERILIZING(CLEANING)
15:16:22 1- RINSING
15:19:52 2- RINSING
15:25:46 DRYING
15:30:36 STERILIZING
 5 MINUTES AT 59°C
15:30:36 COMPLETE

[ PRINT ]
[ CLOSE ]

103

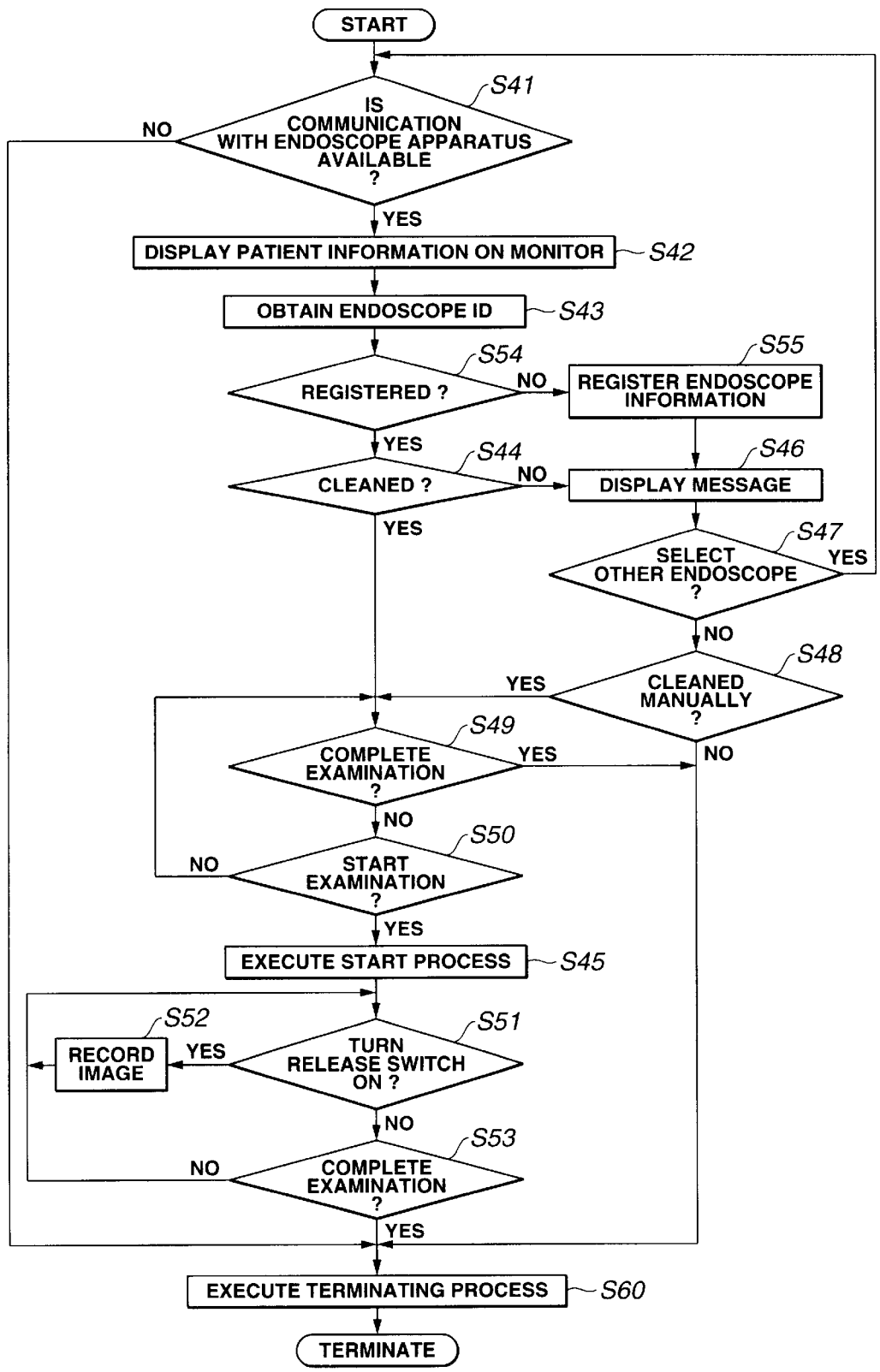

NO ENDOSCOPE INFORMATION FROM CLEANING APPARATUS ABOUT THIS ENDOSCOPE.
IF YOU WANT TO USE THIS ENDOSCOPE, SELECT FOLLOWING OPTIONS.

ENDOSCOPE 1:XXXX OR ENDOSCOPE 2:XXXX

● CLEANED MANUALLY

○ SELECT OTHER ENDOSCOPE

[ OK ]   [ CANCEL ]

ENDOSCOPIC IMAGE FILING SYSTEM FOR MANAGING CLEANING INFORMATION OF ENDOSCOPE WITH IMAGE INFORMATION

This application claims benefit of Japanese Applications No. 2000-140765 filed in Japan on May 12, 2000 and No. 2000-273792 filed in Japan on Sep. 8, 2000, the contents of which are incorporated by this reference.

BACKGROUND OF THE INVENTION

1. Field of the Invention

This invention relates to an endoscopic image filing system having a cleaning apparatus for cleaning an endoscope.

2. Description of the Related Art

An endoscope apparatus which is provided with image pickup means in an endoscope whose elongated insertion section is inserted into a target portion to be examined, such as a coelom and which displays an image of the target portion to be examined, i.e., an endoscopic image, which has been picked up by the image pickup means on a monitor has been utilized conventionally.

Recently, an endoscopic image filing system in which an image filing apparatus for recording endoscopic images is connected to the endoscope apparatus is widely utilized.

In the endoscopic image filing system, when an endoscope switch, such as a release switch, provided on the endoscope apparatus is pressed, a still image of the endoscopic image displayed on the monitor is recorded in the image filing apparatus.

The endoscopic image filing system not only records the endoscopic images, but also can record a variety of information with regard to an endoscopic examination, such as observations and diagnosis for recorded endoscopic images by a doctor or the like, patient information, such as an age and a sex of a patient, a started time and a completed time of the endoscopic examination, and the like.

Incidentally, the endoscope used in the endoscope apparatus must be sterilized/cleaned after using. Recently, a cleaning apparatus is used for a sterilizing/cleaning step, which can automatically be executed by virtue of previously programming the sterilizing/cleaning step. In such the cleaning apparatus, cleaning can also be executed by manual setting without using the programming. Depending on the circumstances, there is a case that a nurse or the like washes the endoscope by using cleaning tools and chemicals (hereinafter refers to as a hand washing).

There is an endoscopic image filing system that can reserve endoscopic examinations performed by the endoscope apparatus. In such a reservation, subjects of reservation information includes information on an endoscope suitable for the examination as well as information on a patient, an examination date, an examination room to be used and so forth.

Plural kinds of endoscopes are provided for one endoscopic apparatus so as to be used selectively depending on an examination target or a content of an examination. In a hospital constructing an endoscopic image filing system or the like a plurality of endoscopes are often prepared for each kind for the reservation of the examination.

The information on the reservation of the examination in the endoscopic image filing system includes the information on the endoscope to be used, as described above, however the endoscope can not be used if the endoscope has yet not been sterilized/cleaned. Conventionally, whether the reserved endoscope has already been sterilized, cleaned or not, cannot be recognized until immediately before the examination. If the reserved endoscope has never been cleaned, one must either look for the same kind of an endoscope as the reserved endoscope or clean the unclean endoscope. Therefore, the problem that the examination cannot be performed efficiently in spite of reserving arises.

OBJECT AND SUMMARY OF THE INVENTION

An object of the present invention is to provide an endoscopic image filing system in which an endoscope is sterilized/cleaned reliably and an endoscope examination can be performed efficiently.

Another object of the invention is to provide an endoscopic image filing system in which a designated endoscope can be sterilized/cleaned reliably before examination so that an endoscope examination can be executed efficiently.

A still another object of the invention is to provide an endoscopic image filing system in which an endoscope can be sterilized/cleaned reliably, the reserved endoscope can be used for another examination during an interval from a reservation time to an examination time, and an endoscope examination can be executed efficiently.

A further object of the invention is to provide an endoscopic image filing system in which a plurality of endoscope can be sterilized/cleaned reliably, frequencies of use of the endoscopes can be averaged, and endoscope examinations can be executed efficiently.

A still further object of the invention is to provide an endoscopic image filing system in which other medical image data, such as an ultrasonic image, a CT (computerized tomography) image and an MRI (magnetic resonance imaging) image, can be managed collectively based on patient information and so forth, as well as an endoscope can be sterilized/cleaned reliably, and an endoscope examination can be executed efficiently.

An endoscopic image filing system according to the present invention comprises an endoscope apparatus for inserting an endoscope having peculiar information into a coelom, to pick up an image of a region to be observed and generate an endoscopic image, and an image filing apparatus for recording the endoscopic image, cleaning information from a cleaning apparatus for cleaning the endoscope, and the peculiar information.

The other futures and advantages of the present invention will be apparent with the following description, sufficiently.

BRIEF DESCRIPTION OF THE DRAWINGS

FIGS. 1 to 17 show a first embodiment of the present invention.

FIG. 1 is a schematic diagram showing a configuration of an endoscopic image filing system;

FIG. 2 is a schematic diagram showing a configuration of an endoscope apparatus shown in FIG. 1;

FIG. 3 is a block diagram showing a configuration of an image filing apparatus shown in FIG. 1;

FIG. 4 is a block diagram showing a configuration of a cleaning apparatus shown in FIG. 1;

FIG. 5 is an explanatory diagram illustrating schematically a structure of screens of the image filing apparatus shown in FIG. 3;

FIG. 6 is a flowchart illustrating an example of an entire flow of an operation of the image filing apparatus shown in FIG. 3;

FIG. 7 is a flowchart illustrating a flow of a sterilizing/cleaning step of the cleaning apparatus shown in FIG. 4;

FIG. 8 is a diagram showing a display screen for editing the examination information of FIG. 5;

FIG. 9 is a flowchart illustrating a flow of a reservation of an examination using the display screen for editing the examination information shown in FIG. 8 in the image filing apparatus;

FIG. 10 is a diagram showing an endoscope list window displayed during the process of FIG. 9;

FIG. 11 is a diagram showing an endoscope registering window for registering a new endoscope displayed while the process of FIG. 9;

FIG. 12 is a diagram showing a first message window displayed during the process of FIG. 9;

FIG. 13 is a diagram showing a second message window displayed during the process of FIG. 9;

FIG. 14 is a diagram showing an endoscope cleaning history window displayed during the process of FIG. 9;

FIG. 15 is a flowchart illustrating a flow of an examination by the image filing apparatus shown in FIG. 3;

FIG. 16 is a diagram showing a third message window displayed during the process of FIG. 9;

FIG. 17 is a diagram showing an examination performing screen shown in FIG. 5.

DETAILED DESCRIPTION OF THE PREFERRED EMBODIMENTS

First Embodiment

Figure 1:
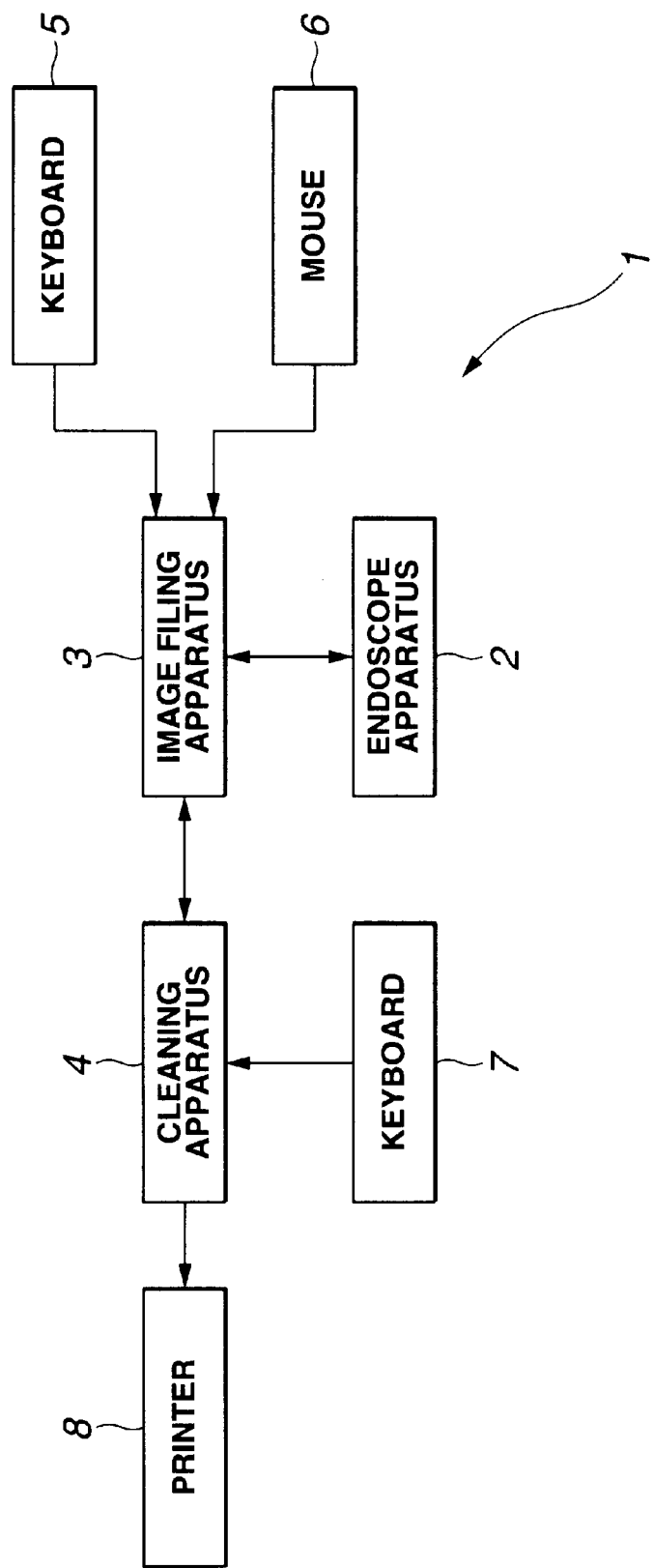

As shown in FIG. 1, an endoscopic image filing system 1 according to the present embodiment mainly comprises an endoscope apparatus 2 performing an endoscopical examination by way of an endoscopic image, an image filing apparatus 3 connected with the endoscope apparatus 2 for recording required endoscopic images, and a cleaning apparatus 4 for sterilizing/cleaning an endoscope used in the endoscope apparatus 2. The image filing apparatus 3 comprises a keyboard 5 and a mouse 6 for inputting and setting a variety of data. The cleaning apparatus 4 comprises a keyboard 7 for inputting data and a printer 8 for printing a sticker or the like which indicates that an endoscope has been cleaned and is stuck on the endoscope which has been cleaned, for example. The cleaning apparatus 4 is capable of transmitting cleaning information to the image filing apparatus 3.

Figure 2:
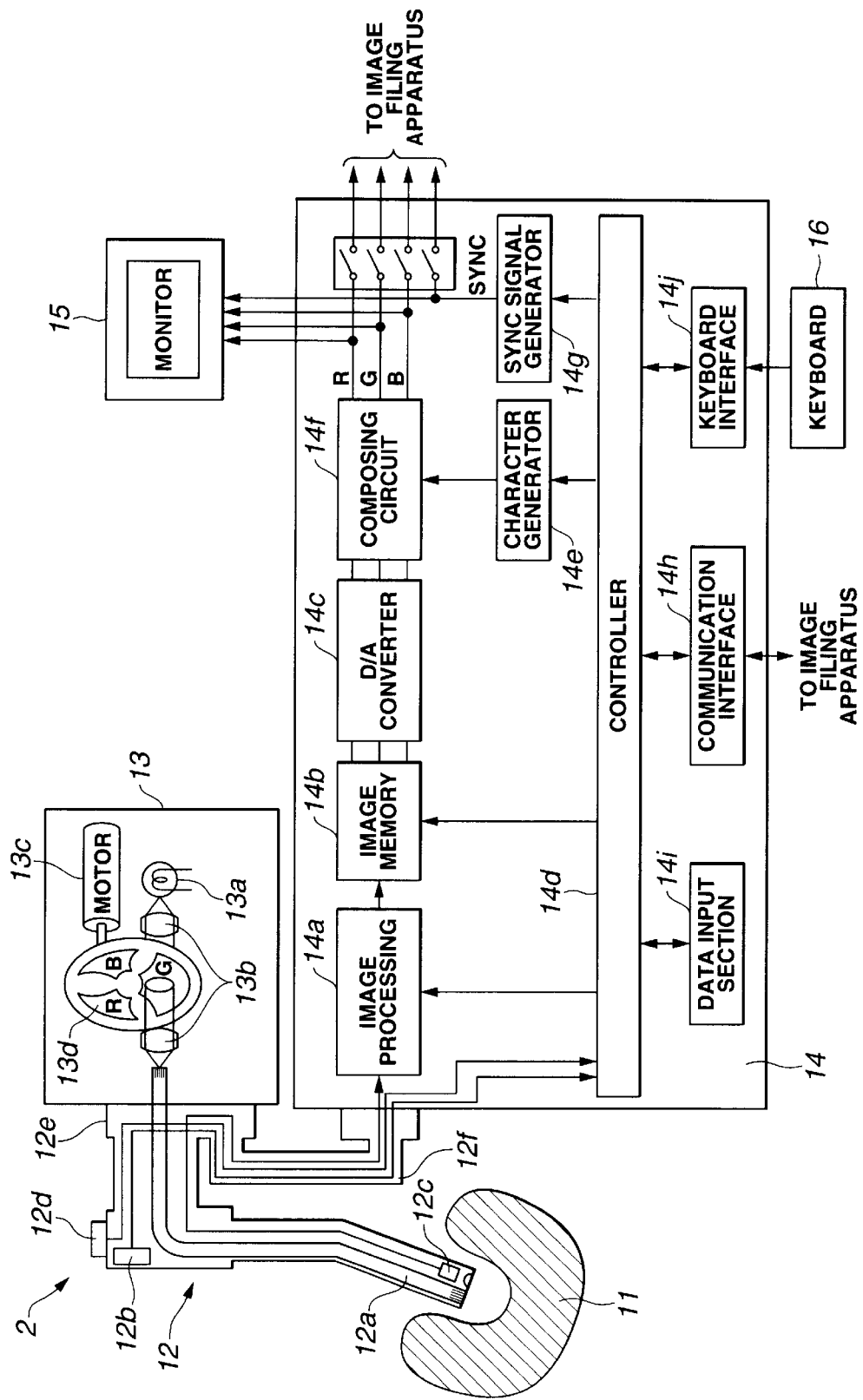

As shown in FIG. 2, the endoscope apparatus 2 comprises an endoscope 12 to be inserted into a coelom for picking up an image of a target portion 11 to be examined, a light source apparatus 13 for supplying illuminative light to the endoscope 12, an image generating apparatus 14 for processing an image signal from the endoscope 12 to generate an endoscopic image, a monitor 15 for displaying the endoscopic image generated by the image generating apparatus 14, a keyboard 16 for inputting data, and so forth.

In the endoscope 12, a light guide 12a for transmitting the illuminative light, which illuminates the target portion 11, from a proximal end of the endoscope 12 to a distal end of a insertion portion thereof is provided and the proximal end of the light guide 12a is connected to the light source apparatus 13. In an operation portion located at a proximal end side of the insertion portion, an EEPROM (electronic erasable programmable read only memory) 12b which is a rewritable nonvolatile memory is provided. In this EEPROM 12b, a management number in a hospital as well as an endoscope ID (identifier), which is peculiar information of the endoscope, are stored rewritably.

In the light source apparatus 13, light emitting means 13a such as a lamp for emitting the illuminative light is provided. The illuminative light emitted from the light emitting means 13a is converged by a converging optical system 13b and enters the light guide 12a.

In a light path of the converging optical system 13b, a rotary disk provided with three optical filters 13d of red, green and blue colors (denoted as R. G and B in FIG. 2) rotated by a motor 13c is disposed, thereby switching colors of the illuminative light which illuminates the target portion 11 in a time divisional manner.

On the other hand, in the distal end of the insertion portion of the endoscope 12, an image pickup apparatus 12c comprising solid-state image picking up elements for picking up the target portion 11 such as CCDs is disposed.

The endoscope 12 is connected to the light source apparatus 13 by a connector 12e and connected to the image generating apparatus 14 by a universal cable 12f. The EEPROM 12b and the image pickup apparatus 12c are electrically connected to the image generating apparatus 14 by way of the universal cable 12f.

Image signals of the target portion 11 picked up by the image pickup apparatus 12c are inputted to an image processing portion 14a in the image generating apparatus 14 where they are subjected to an image processing such as color enhancing process, for example, and stored as image data in an image memory 14b temporally and sequentially.

The image data stored in the image memory 14b is inputted to a D/A (digital to analog) converter 14c so as to be D/A converted, and the D/A converter 14c outputs image signals in an RGB format.

The image processing section 14a, the image memory 14b and so forth are controlled to operate by a controller 14d as control means for each section within the image generating apparatus 14.

The image signal output from the D/A converter 14c is mixed with an image signal output from a character generator 14e, described later, in a composing circuit 14f, an image signal in the RGB format outputted from the composing circuit 14f is inputted to the monitor 15, and the image of the target portion to be examined is displayed on the monitor 15. In this case, a sync signal generator 14g controlled by the controller 14d generates the sync signal (denoted as SYNC in FIG. 2) provided to the monitor 15.

From the controller 14d, character information is inputted to the character generator 14e, and the character generator 14e converts the inputted character information to the image signal and outputs it. That is, on the screen of the monitor 15, a mixed image of the image of the target portion and the character information is displayed and a variety of messages can be provided to a user of the endoscope apparatus 2.

The image signal output from the composing circuit 14f is outputted to the image filing apparatus 3 so as to be displayed on the image filing apparatus 3 as well as outputted to the monitor 15.

On the endoscope 12, endoscope switches 12d including a release switch for inputting an instruction to record an image, and a start/complete switch pressed at the beginning and terminating of the endoscope examination are provided, and the controller 14d can detect the status of the endoscope switches 12d.

The controller 14d can also transmit and receive information to and from the image filing apparatus 3 by way of a communication interface section 14h, for example, in a well-known RS-232C format.

Thus, the endoscope apparatus 2 can transmit a variety of statuses, such as the states of the switches 12d, of the endoscope apparatus 2 to the image filing apparatus 3. The endoscope apparatus 2 can also receive a variety of messages from the image filing apparatus 3 and can display the received message on the monitor 15 by way of the character generator 14e and so forth.

A data input section 14i is provided for storing and inputting data and an instruction inputted from the keyboard 16 to the controller 14d. A keyboard interface section 14j is provided for detecting presence/absence of an input from the keyboard 16.

Figure 3:
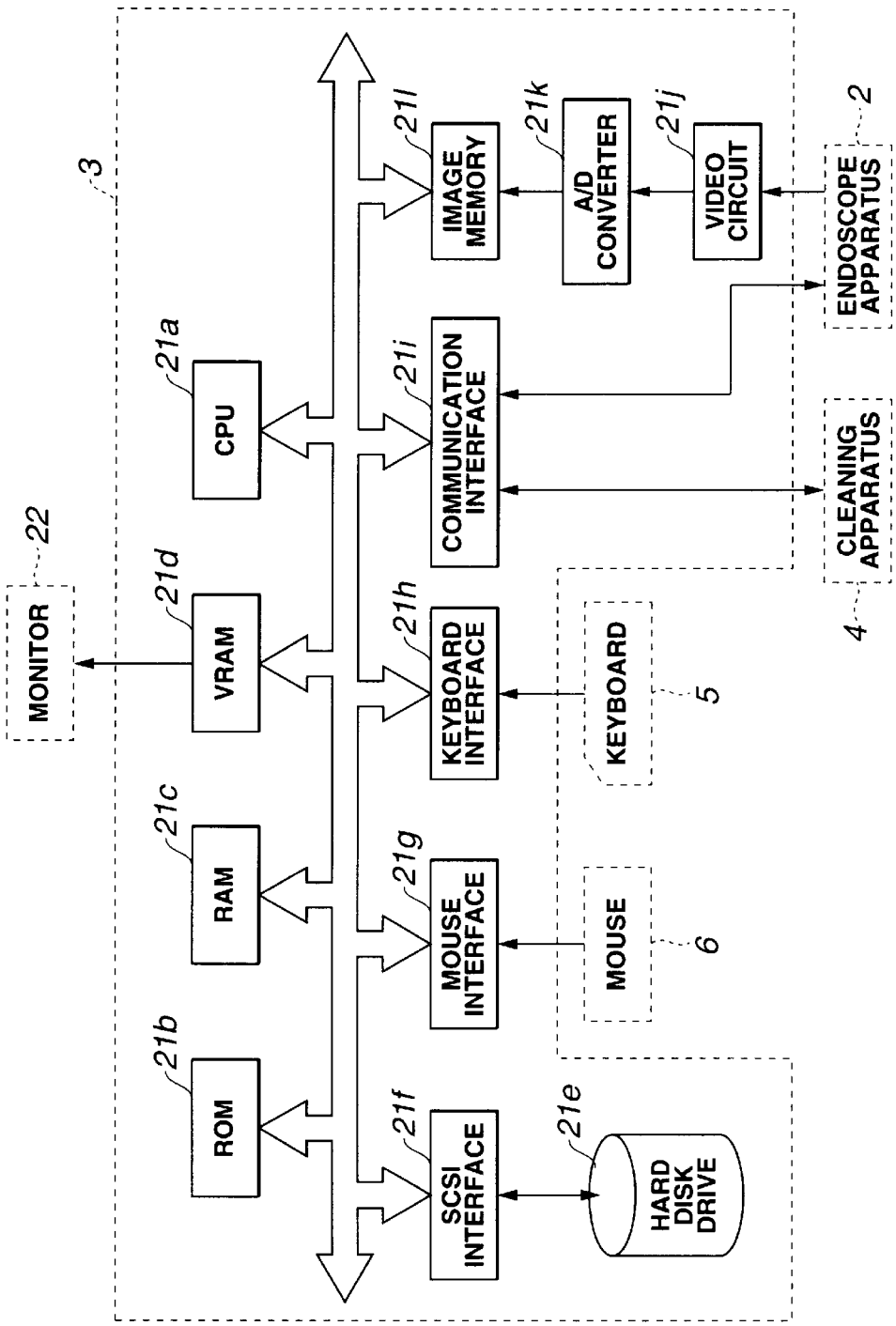

As shown in FIG. 3, the image filing apparatus 3 comprises a CPU (central processing unit) 21a, which is main control means, for controlling respective sections, a ROM (read only memory) 21b in which a program to operate the CPU 21a, a message to be displayed on the monitor 22, and so forth are stored, a RAM (random access memory) 21c to be used as a work area of the CPU 21a and a temporal storage area of a variety of data, a VRAM (video RAM) 21d for temporally storing the image data outputted to a monitor 22, a hard drive 21e for storing the image data and a variety of data, a SCSI (small computer system interface) interface section 21f for transmitting and receiving data to and from the hard drive 21e, respectively, by way of a well-known SCSI format, a mouse interface section 21g for detecting an input from the mouse 6, a keyboard interface section 21h for detecting an input from the keyboard 5, a communication interface section 21i in accordance with a well-known RS-232C format, for example, for transmitting and receiving a variety of data to and from the endoscope apparatus 2 and the cleaning apparatus 4, a video circuit 21j, which is an interface circuit for inputting the image signal outputted from the endoscope apparatus 2, an A/D (analog to digital) converter section 21k for A/D converting the image signal inputted from the video circuit 21j, an image memory 21l for temporally storing the image data outputted from the A/D converter section 21k, and so forth.

Thus, the image filing apparatus 3 can display the image data obtained from the endoscope apparatus 2 on the monitor 22 and store the image data on the hard drive 21e.

The image filing apparatus 3 can obtain the status of the endoscope switch 12d and assign the process by the CPU 21a corresponding to the status of the endoscope switches 12d, for example, either to record the image or record the start and terminate time of the examination. The message from the image filing apparatus 3 can be transmitted to the endoscope apparatus 2.

The image filing apparatus 3 is configured such that an operator inputs the data or the instruction by the keyboard 5 or the mouse 6 in accordance with respective screens displayed on the monitor 22, and the CPU 21a controls the respective sections to perform/respective processes in accordance with the inputted data or instruction. Thus, the image filing apparatus 3 is configured for performing respective processes in accordance with a flow of the screens which are displayed on the monitor 22.

Figure 4:
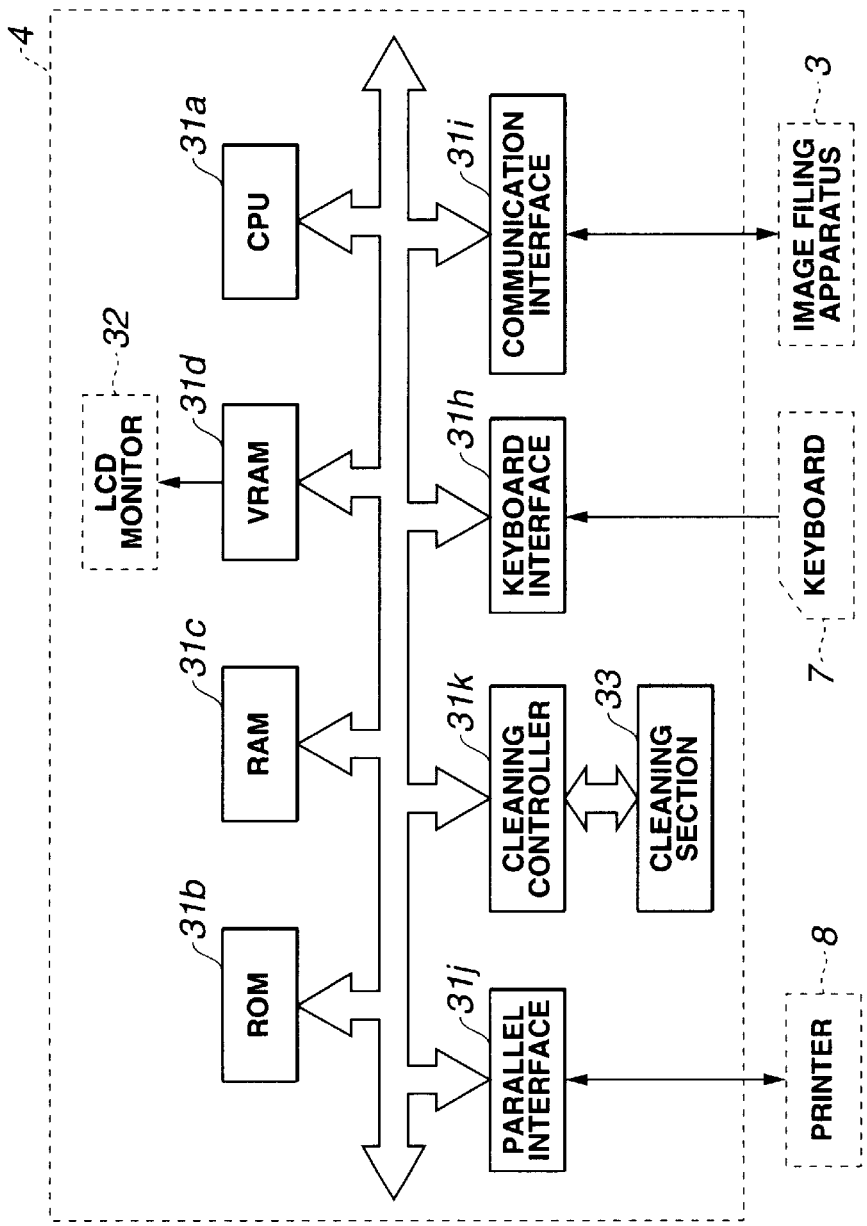

As shown in FIG. 4, the cleaning apparatus 4 comprises a CPU 31a, which is a main control means, for controlling respective sections, a ROM 31b in which a program to operate the CPU 31a, a message to be displayed on an LCD monitor 32, and so forth are stored, a RAM 31c to be used as a work area of the CPU 31a and a temporal storage area of a variety of data, a VRAM 31d for temporally storing the image data outputted to the LCD monitor 32, a keyboard interface section 31h for detecting an input from the keyboard 7, a communication interface section 31i in accordance with the well-known RS-232C format, for example, for transmitting and receiving a variety of data to and from the image filing apparatus 3, a parallel interface section 31j for outputting a data to the printer 8, a cleaning control section 31k for controlling a cleaning section 33 which sterilizes and cleans the endoscope and so forth.

Figure 5:
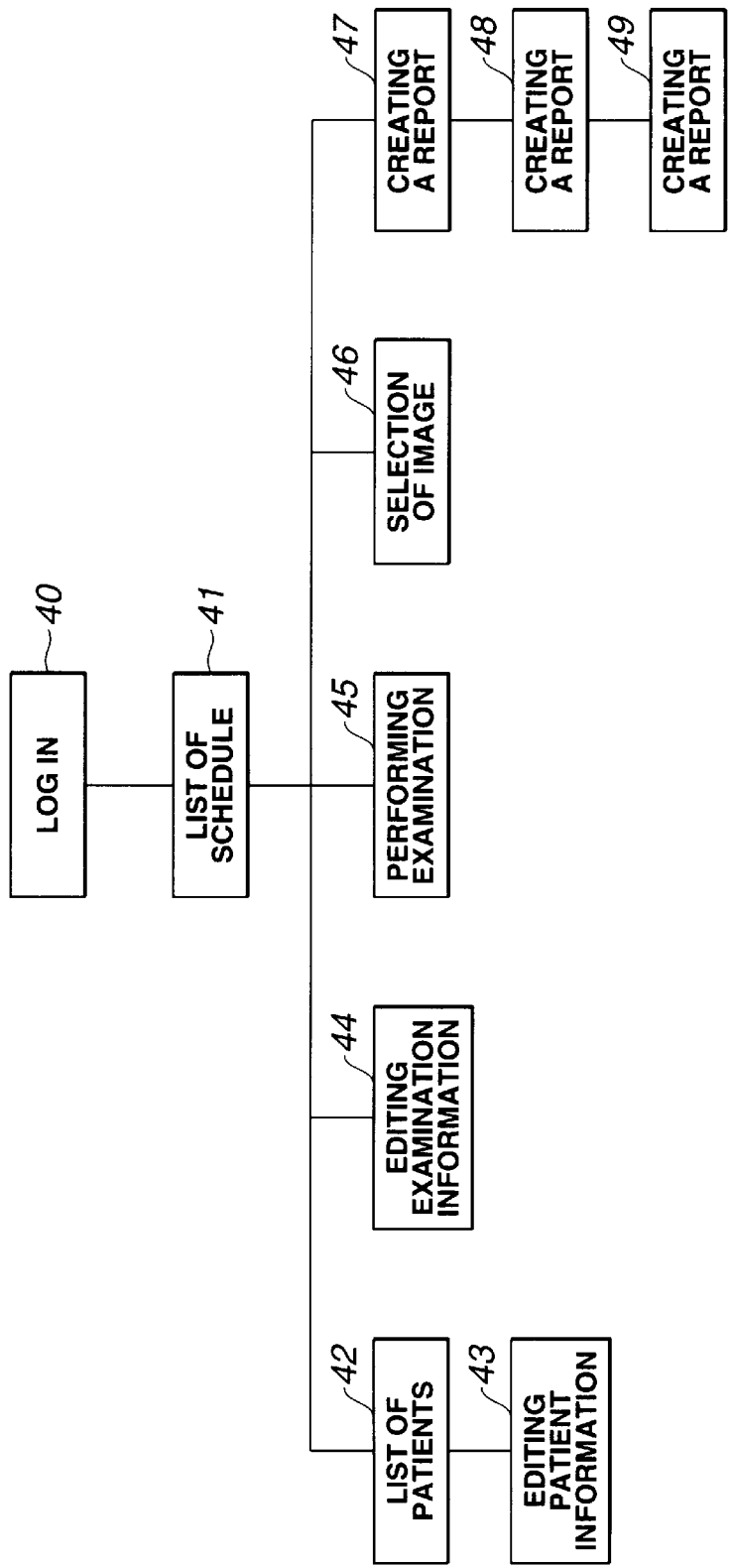

Referring to FIG. 5, a schematic configuration of screens of the image filing apparatus 3 will be described.

At first, when the image filing apparatus 3 is actuated, a log in screen 40 for certifying an operator is displayed on the monitor 22. If the operator is certified on the log in screen 40, a schedule screen 41 for displaying a list of examination schedules and the like is displayed on the monitor 22.

A patient list screen 42 for displaying a list of patient information can be called from the schedule screen 41. A patient information editing screen 43 for newly registering patient information or editing the patient information already registered can be called from the patient list screen 42.

An examination information editing screen 44 for newly registering examination information so as to reserve the examination or editing the examination information already registered can be called from the schedule screen 41.

An examination performing screen 45 connecting with the endoscope apparatus 2 to perform an examination and capture the image from the endoscope apparatus 2 can also be called from the schedule screen 41.

An image posting screen 46 for selecting images from the captured images for an examination report to be created can also be called from the schedule screen 41.

A report writing screen 47 which is one of the screens for writing an examination report can also be called from the schedule screen 41. Report writing screens 48 and 49 that have the different functions respectively for writing an examination report are transitioned from the report writing screen 47.

Next, an operation of the present embodiment thus configured will now be described.

Figure 6:
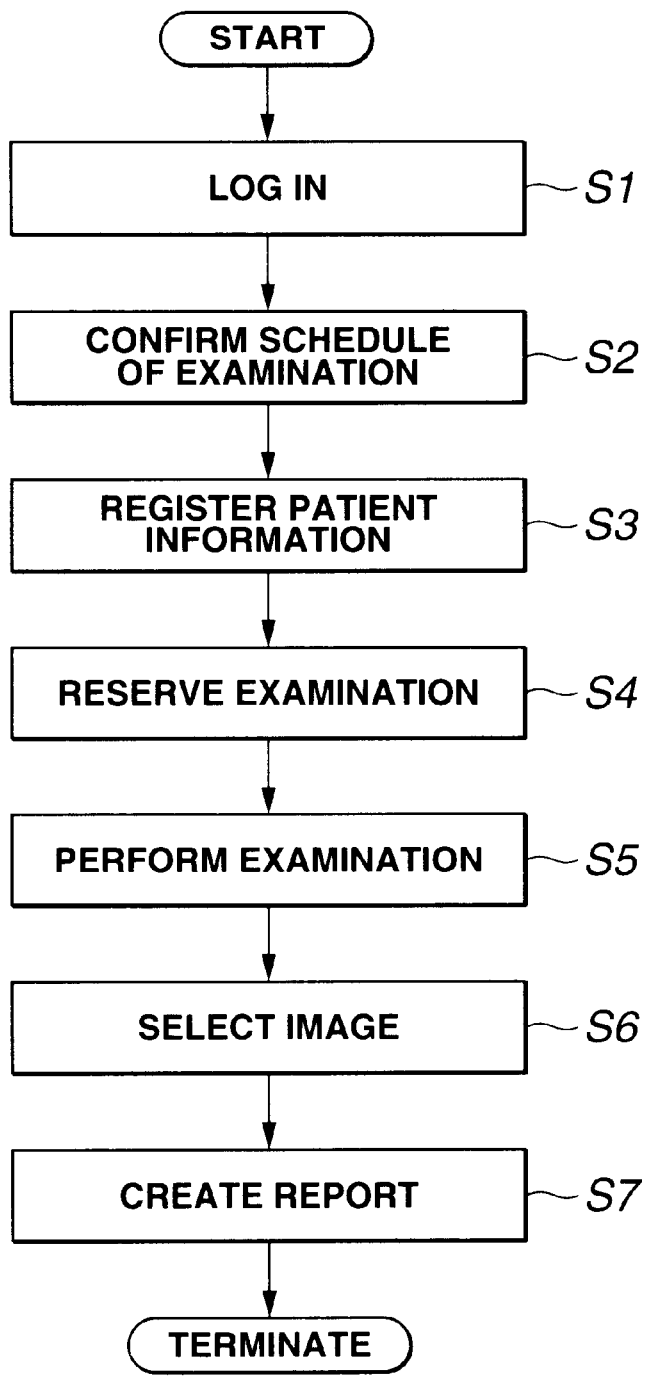

Referring to FIG. 6, an example of an entire flow of the operation of the image filing apparatus 3 will be described. At first, when the image filing apparatus 3 is actuated, the log in screen 40 is displayed at step S1, where the certification of the operator is performed. If the operator logs in after the certification, the schedule screen 41 is displayed for confirming the examination schedule at step S2.

Next, if the patient to be examined is a new patient, the patient list screen 42 and the patient information editing screen 43 are called and the patient information is registered, at step S3. At step S4, the examination information editing screen 44 is called and the new reservation of the examination is inputted.

Next, at step S5, the examination performing screen 45 is called, and the examination is performed by the endoscope apparatus 2 connected to the image filing apparatus 3, and then images obtained from the endoscope apparatus 2 are recorded on the image filing apparatus 3. At step S6, the image posting screen 46 is called, and images to be referred from the written examination report are selected from the images obtained during the examination. At step S7, the report writing screens 47, 48 and 49 are called and the examination report is created. An example of an entire flow of the operation is described hereinbefore.

Thus, the endoscope examination is performed by the endoscope apparatus 2 and the endoscope 12 used in the examination is sterilized/cleaned by the cleaning apparatus 4.

Figure 7:
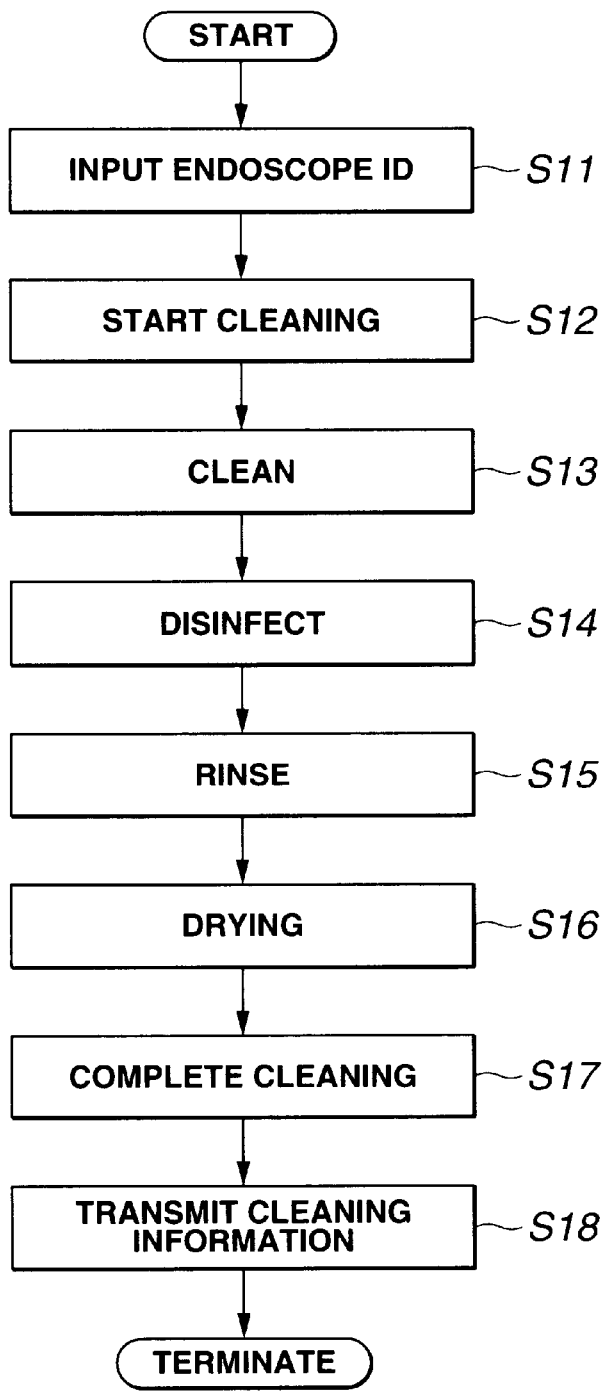

In the cleaning apparatus 4, the used endoscope 12 is stored in the cleaning section 33, and sterilizing/cleaning of the endoscope 12 is performed by the cleaning control section 31k. Then, the cleaning control section 31k sterilizes and cleans the endoscope 12 based on a predetermined cleaning program executed in the CPU 31a. For example, as shown in FIG. 7, at step S11, the endoscope ID, which is the peculiar information of the endoscope, is inputted from the keyboard 7. Alternatively, the CPU 31a may recognize the endoscope ID, by using a transponder or the like so as to read out the endoscope ID.

Next, at step S12, the CPU 31a starts the cleaning/sterilizing process in accordance with the predetermined program. The cleaning apparatus 4 transmits the information, which indicates starting of the cleaning/sterilizing process, as well as the endoscope ID obtained from the keyboard 7, the transponder or the like, to the image filing apparatus 3. The image filing apparatus 3 records the starting time of cleaning/sterilizing of the corresponding endoscope associated with the registered endoscope ID in a manner later described into the database. In this cleaning/sterilizing process, first a leakage test for confirming airtightness of the endoscope 12 is performed. Further, the cleaning/sterilizing process comprises a cleaning step of step S13, a sterilizing step of step S14, a rinsing step of step S15, and a drying step of step S16, thereby terminating the cleaning/sterilizing process at step S17.

Information on starts of the respective steps and information on termination of the cleaning/sterilizing process are transmitted to the image filing apparatus 3 in a manner associated with the endoscope ID, and the image filing apparatus 3 records the start times of the respective steps of the corresponding endoscope, and the termination time of the cleaning/sterilizing process in a manner associated with the endoscope ID on the database.

Alternatively, the cleaning/sterilizing process may be terminated at step S17, and the start times of the respective steps and the termination time of the cleaning/sterilizing process may be transmitted to the image filling apparatus 3 in a manner associated with the endoscope ID, and then the process may be terminated at step S18. At this time, the image filing apparatus 3 records the start time of the respective steps and the termination time of the cleaning/sterilizing process for the corresponding endoscope in a manner associated with the endoscope ID on the database.

On the other hand, the endoscopic examination in the endoscopic image filing system 1 is managed by the image filing apparatus 3 based on the reservation of the examination. The reservation of the examination is performed with the examination information editing screen 44 (see FIG. 5) as shown in FIG. 8. That is, the examination information editing screen 44 shown in FIG. 8 is the screen for either newly registering or updating the examination information record. In the examination information editing screen 44, a region 61a for inputting each data item included in the examination information record is located.

In the region 61a, for example, an input box 61aa for inputting an examination room, an input box 61ab for inputting an examination date, an input box 61ac for inputting an examination starting time, an input box 61ad for inputting an examination terminating time, an input box 61ae for inputting a full name of a patient, a region 61ag including input boxes for inputting names of persons in charge of an examination such as a doctor and nurses, an input box 61ah for inputting a reception date of an agreement for an examination from a patient, a region 61ai including input boxes for inputting such as model numbers of the endoscopes used for an examination and so forth, an input box 61aj for inputting such as an examination result and the like are located.

In the bottom portion of the examination information editing screen 44, an undo button 61c for returning the information in the region 61a back to the state at the point of calling the examination information editing screen 44 when clicked, an OK button 61d for newly registering or updating the examination information record and terminating the examination information editing screen 44 when clicked, and a cancel button 61e for canceling without newly registering or updating the examination information record and terminating the examination information editing screen 44 when clicked, and so forth.

In the examination information editing screen 44, when the examination starting time is inputted in the input box 61ac, the examination terminating time is estimated by adding a standard time duration required for an examination recorded in the image filing apparatus 3 previously and therefore the examination terminating time is automatically inputted in the input box 61ad.

The flow of the reservation of an examination using the examination information editing screen 44 now will be described with referenced to the flowchart shown in FIG. 9.

Figure 9:
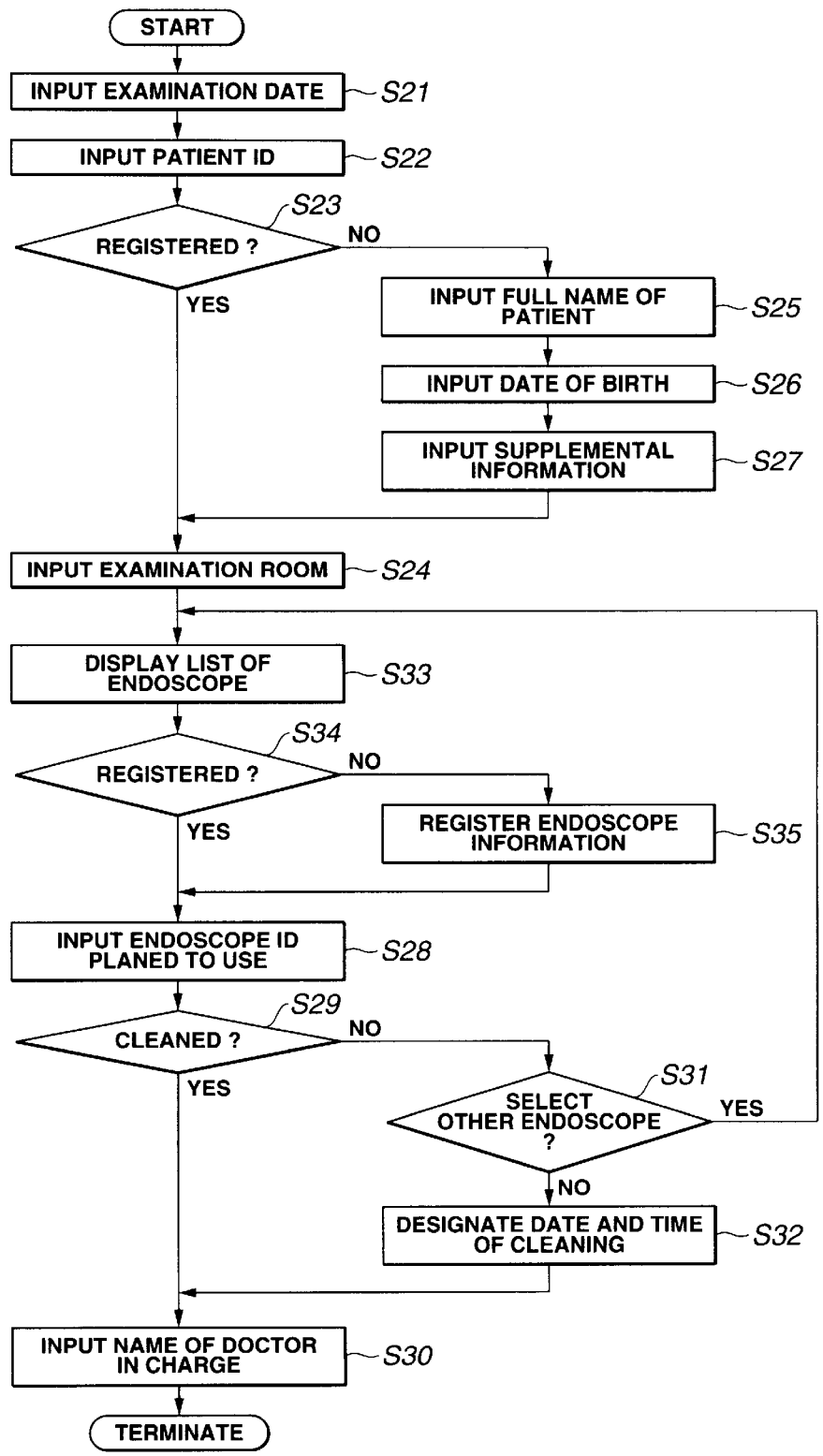

As shown in FIG. 9, at step S21, first the examination date intended to be reserved is inputted and, at step S22, the patient ID is inputted. Then, at step S23, whether or not the inputted patient has been already registered is determined. When it has been registered, the process jumps to step S24, and when it has not been registered yet, the process advances to step S25.

At step S25, a full name of the patient is inputted, thereafter at step S26, a date of birth, and, at step S27, supplemental information are inputted respectively, and the process advances to step S24.

At step S24, an examination room which will be used is inputted. Then the process advances to step S33 and the endoscope list window 100 is displayed on the monitor 22 as shown in FIG. 10. In this window, the list of the endoscopes which have been already registered is displayed. In the endoscope list window 100, an add button 100a for adding a new endoscope, an edit button 100b for changing registered contents of the registered endoscope, and a delete button 100c for deleting the registered endoscope are located. The process advances to step S34, if the endoscope intended to be used has already been registered, at step S28, the endoscope ID of the endoscope intended to be used is selected from the list and is inputted.

If the endoscope intended to be used has not been registered, for example a new endoscope is used, the add button 100a is clicked so that the endoscope registration window 105 as shown in FIG. 11 is opened, and thereby information of the endoscope is inputted and added to the list of the endoscope at step S35. The inputted information includes, for example, a type of the endoscope, the endoscope ID, a type of the examination, and a management number of the hospital. When the registration is completed, the process advances to step S28, and the endoscope ID of the newly added endoscope is selected from the list and is inputted.

Then, at step S29, the database is referred to and whether or not the endoscope selected from the list has already been cleaned is determined. In this determination, at first, the terminated time of the last cleaning/sterilizing process which has been recorded for each endoscope by the above described manner is read out, and then the examination starting time of the last examination using the endoscope which is recorded in the later described manner is read out. If the terminated time of the last cleaning/sterilizing process is later than the examination starting time of the last examination, it is determined that the endoscope has already been cleaned, and the process advances to step S30. When the terminated time of the last cleaning/sterilizing process is earlier than the examination starting time of the last examination, it is determined that the endoscope has not been cleaned, and the process advances to step S31.

Figure 12:
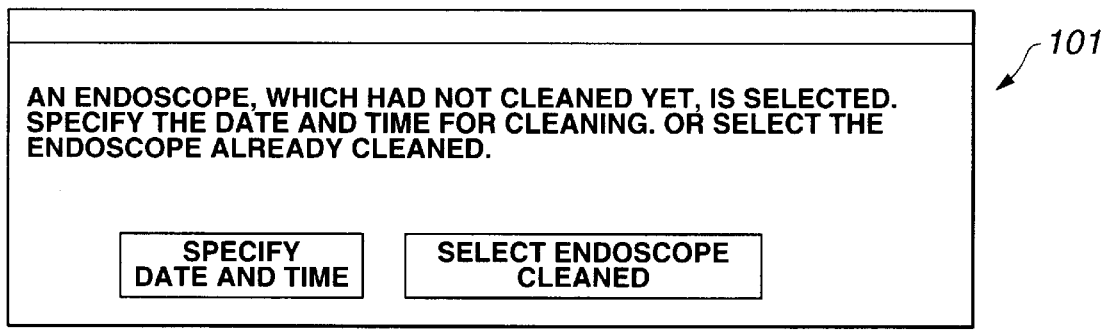
Figure 13:
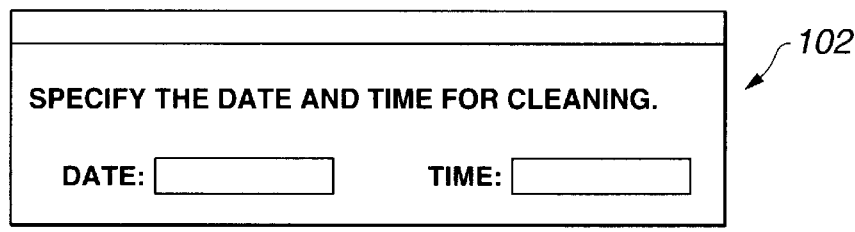

At step S31, by displaying a first message window 101, as shown in FIG. 12, on the monitor 22, a determination is made about whether or not another endoscope is to be selected. If another endoscope is to be selected, the process returns back to step S33. Hereafter through the similar process, when it is determined that the endoscope has been cleaned at step S29, the process advances to step S30. At step S32, when the selected endoscope is to be used as it is, by displaying a second message window 102, as shown in FIG. 13, a cleaning date is designated, and thereafter the process advances to step S30.

Then, at step S30, a name of the doctor in charge of the examination is inputted and the reservation process is terminated.

Thus, the image filing apparatus 3 stores a variety of the reservation data as the database onto the hard drive 21e.

Since the data formed in the database includes the information having relation to the cleaning and sterilizing process transmitted from the cleaning apparatus 4 other than the reservation data as described above, cleaning/sterilizing conditions of the endoscope 12 can be collectively managed. Namely, the image filing apparatus 3 can collectively manage the cleaning/sterilizing conditions of the endoscope 12 with an endoscope cleaning history window 103 as shown in FIG. 14 by way of cleaning date, a cleaning starting time, a cleaning terminating time, a scope type indicating a type of the endoscope, a management number of the endoscope, a serial number of the cleaning apparatus 4, a cleaning program, supplemental information (explanation), and so forth. Further, in the image filing apparatus 3, a process of the cleaning program can also be recognized time divisionally.

In the endoscopic image filing system 1, when an endoscopic examination reserved by the examination information editing screen 44 is performed, as shown in FIG. 15, at step S41 a determination is made about whether or not a communication with the endoscope apparatus 2 is available. Namely, the system determines whether or not the endoscope apparatus 2 has been connected to the system 1. When the communication with the endoscope apparatus 2 is not available, then the process jumps to step S60 so as to perform the termination process and terminate the process.

When the communication with the endoscope apparatus 2 becomes available, at step S42, the patient information is retrieved from the hard drive 21e and displayed on the monitor 15. Then, at step S43, the endoscope ID is obtained from the EEPROM 12b of the endoscope 12 connected to the image generating apparatus 14, and at step S54, a confirmation is made about whether the endoscope 12 has been registered at the database or not. When the endoscope 12 has been registered at the database, the process advances to step S44. When the endoscope 12 has not been registered at the database, the process advances to step S55 so that the endoscope is registered at the database with the same operation of the reservation of the examination of step S35 described above. At this time, the name of the endoscope type and the endoscope ID are registered automatically. Since this endoscope does not have any information on cleaning, this endoscope is regarded not to be cleaned and process advances to step S46.

At step S44, a determination is made about whether the endoscope corresponding to the obtained endoscope ID has been cleaned or not, based on both the examination starting time of the last examination and the terminated time of the last cleaning/sterilizing process recorded on the hard drive 21e, similar to an operation of the reservation of the examination described above.

At step S44, when it is determined that the endoscope corresponding to the obtained endoscope ID has been cleaned, the process advances to step S49. At step S44, when it is determined that the endoscope corresponding to the obtained endoscope ID has not been cleaned, the process advances to step S46.

At step S46, since it is determined that the connected endoscope has not been cleaned, a third message window 104 as shown in FIG. 16 is displayed so that a determination is made about whether another endoscope is selected by the message window 104, or the endoscope has been manually cleaned (or cleaned by hand washing). When, at step S47, another endoscope is selected, the image generating apparatus 14 is turned off, the endoscope is changed to the selected endoscope, thereafter the image generating apparatus 14 is turned on again, and the process returns to step S41. Alternatively, if it is confirmed that the endoscope connected to the image generating apparatus 14 has been manually cleaned and sterilized without using the cleaning apparatus 4, at step S48, "Cleaning Manually" is selected by the message window 104 and the process advances to step S49. If neither a selection of another endoscope nor, manually cleaning (or hand washing) have been selected, the process advances to step S60 so that the terminating process is performed and the process is terminated.

Figure 17:
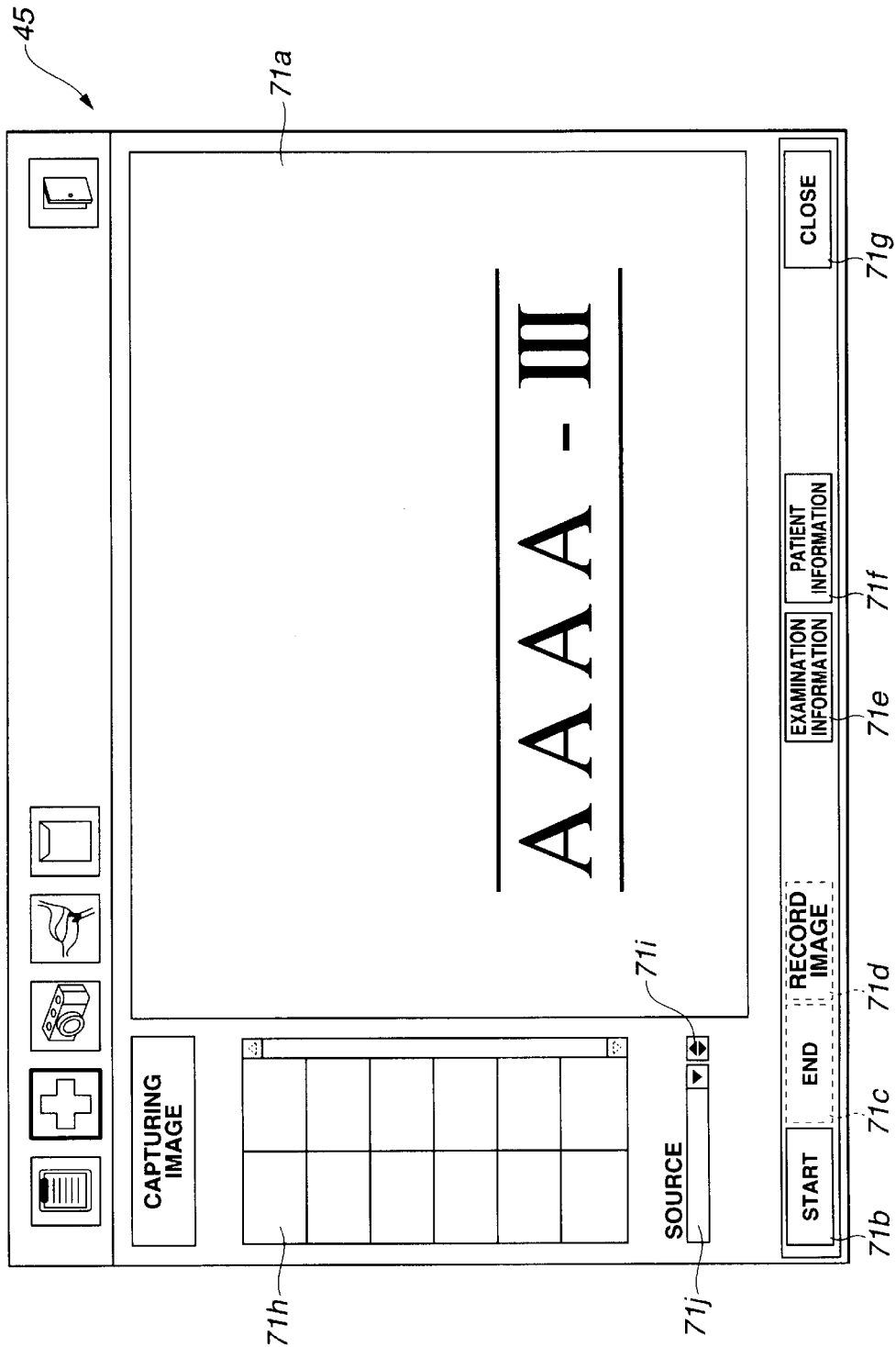

An examination performing screen 45 shown in FIG. 17 is a screen for operating the image filing apparatus 3 side when the examination using the endoscope apparatus 2 is performed.

In the examination performing screen 45, an endoscopic image display area 71a for displaying the same image as shot by the endoscope apparatus 2, i.e., displayed on the monitor 15 of the endoscope apparatus 2, is disposed.

The image shot by the endoscope apparatus 2 is outputted from the image generating apparatus 14 of the endoscope apparatus 2, received at the video circuit 21j of the image filing apparatus 3, and thereby transmitted to the image filing apparatus 3.

At the bottom portion of the examination performing screen 45, a start button 71b for acknowledging the start of the examination to the image filing apparatus 3, an end button 71c for acknowledging the completion of the examination to the image filing apparatus 3, a release button 71d for recording in the image filing apparatus 3 an image at the time point of the clicking, an examination data button 71e for calling an examination information reference screen to refer to the examination information during the examination is performed, a patient data button 71f for calling a patient information reference screen to refer to the patient information during the examination is performed, and a close button 71g for terminating the examination performing screen 45 are located.

In the examination performing screen 45, a thumbnail image display area 71h for displaying a plurality of thumbnail images, i.e., a decreased size image by such as curtailing, by recorded by clicking the release button 71d is disposed.

The times when the start button 71b and the end button 71c are clicked, are recorded in the image filing apparatus 3 as the examination started time and examination terminated time, respectively.

Instead of operating the start button 71b, the end button 71c and the release button 71d, the endoscope switch 12d can be used for the same operation. In this case, the signal from the endoscope switch 12d is transmitted through the communication interface section 14h in the endoscope apparatus 2 and the communication interface section 21i to the image filing apparatus 3.

On the other hand, the transmission of the data between the endoscope apparatus 2 and the image filing apparatus 3 is not only performed from the endoscope apparatus 2 to the image filing apparatus 3 but also performed from the image filing apparatus 3 to the endoscope apparatus 2.

Returning to FIG. 15, at step S49, a determination is made about whether the examination completion switch of the endoscope switch 12d (or the end button 71c) has been pressed or not. If the examination completion switch has been pressed, the process is terminated. If the examination completion switch has not been pressed, the process advances to step S50. At step S50, a determination is made about whether the examination start switch (or the start button 71b) has been pressed or not. If the examination start switch has not been pressed, the process returns to step S49. If the examination start switch has been pressed, the process advances to step S45, so that the endoscope apparatus 2 transmits information, which indicates starting of the examination, along with the endoscope ID obtained in step S43 to the image filing apparatus 3. The image filing apparatus 3 records the examination starting time associated with the corresponding endoscope onto the database and the process advances to step S51.

At step S51, a determination is made about whether the release switch of the endoscope switch 12d (or the release button 71d) has been pressed or not. If the release switch has been pressed, the image is recorded at step S52 and the process returns to step S51. If the release switch has not been pressed, at step S53, a determination is made about whether the examination completion switch of the endoscope switch 12d (or the end button 71c) is pressed or not. If the examination completion switch has been pressed, the process advances to step S60 so that the endoscope apparatus 2 transmits information, which indicates completing of the examination, along with the endoscope ID obtained in step S43 to the image filing apparatus 3, and performs the completion process thereby terminating the process. The image filing apparatus 3 records the examination completing time associated with the corresponding endoscope onto the database. If the examination completion switch has not been pressed, the process returns to step S51.

Thus, according to the present embodiment, since the cleaning/sterilizing condition of the endoscope 12 is managed collectively by the information from the cleaning apparatus 4, a determination can be made about on the reservation whether the endoscope to be used has been cleaned or not. If the endoscope to be used has not been cleaned on the reservation, the cleaning also can be reserved so as to complete the cleaning until the date and time of the reservation, thereby making it possible that the designated endoscope is surely sterilized/cleaned before the examination, and the endoscopic examination can be performed effectively.

Even if the reserved endoscope is used by another examination during the time duration from the reservation to the examination and thereby the reserved endoscope has not been cleaned at the reserved examination, by the information from the cleaning apparatus 4 it is recognized that the endoscope has not been cleaned. Consequently, it is easy to determine that another endoscope is substituted for the endoscope, or if the scope has been cleaned manually after last examination, the scope is recognized as an unclear one but it is possible to determine to use the scope by confirming the date of manual cleaning, and the reserved endoscope can be used in another examination during the time duration from the reservation to the examination. Therefore the endoscopic examination can be performed efficiently.

Further, since the frequency of use of the endoscope or the like can be confirmed by the endoscope cleaning history window, the frequency of use of a plurality of the endoscopes can be averaged as well as the information for the examination and the maintenance of the frequently used endoscope. Therefore the endoscope can be used efficiently.

Second Embodiment

Since the second embodiment is almost similar as the first embodiment, there will be described only the different points and the same reference numerals are used as the same components so that the explanation about them is omitted.

Figure 18:
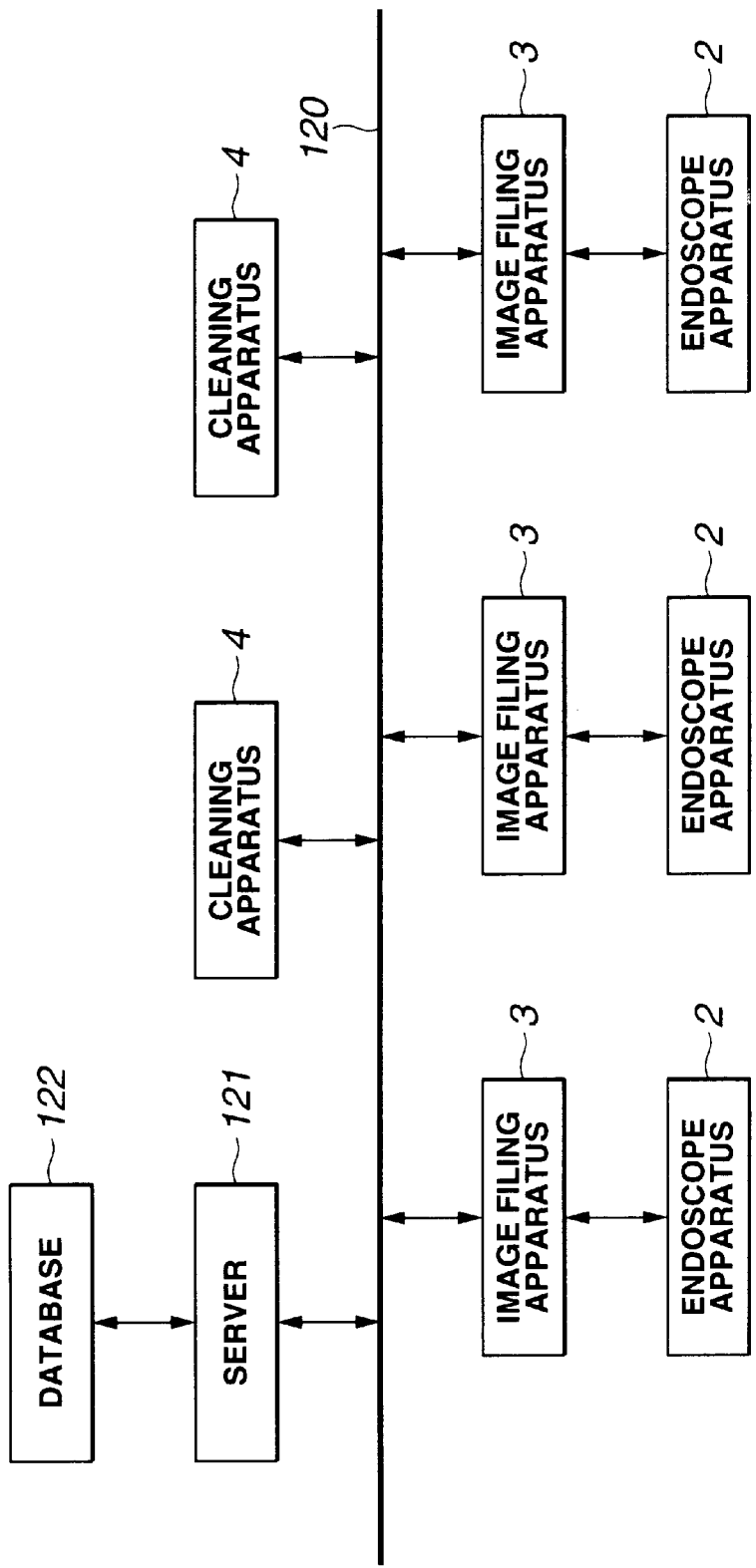
FIG. 18 is a schematic diagram showing a configuration of an endoscopic image filing system according to a second embodiment of the present invention.

In the present embodiment, as shown in FIG. 18, an endoscopic image filing system is connected to a hospital LAN (local area network) 120 constructed in a hospital. A plurality of image filing apparatuses 3 and cleaning apparatuses 4 are connected to the hospital LAN 120, and information obtained from these apparatuses are managed by a server 121.

The image filing apparatus 3 is capable of connecting the endoscope apparatus 2, and endoscopic images obtained by the endoscope apparatus 2 can be recorded and stored in the image filing apparatus 3.

The server 121 nonreversibly or reversibly compresses the endoscope images which are recorded and stored in a plurality of image filing apparatuses 3 onto a large capacity recording apparatus 122, for example, and records and stores the compressed images, as well as records the patient information and the examination information with reference to the endoscopic images, and the management data such as the reservation information as database always updated. The information on sterilizing/cleaning from the cleaning apparatuses 4 are also always updated and recorded onto the large capacity recording apparatus 122 as database.

In the present embodiment, when the reserve information is inputted by image filing apparatus 3 on reserving the examination, the database of the large capacity recording apparatus 122 is retrieved by the server 121 through the hospital LAN 120. As a result, the latest cleaning condition of the endoscope to be used can be recognized.

On the examination, the latest cleaning condition of the endoscope can be recognized by way of the server 121 that retrieves the database of the large capacity recording apparatus 122 through the hospital LAN 120.

Thus the same effect as that of the first embodiment can be obtained in this embodiment. Further, since the endoscopic images are managed by using the hospital LAN 120 in this embodiment, other medical image information, such as an ultrasonic image, a CT image, an MRI image, and so forth, can be managed by the server 121 collectively based on the patient information.

It is apparent that in this invention a variety of different embodiments can be configured widely based on this invention without departing from the spirits and scope of the invention. This invention is not limited with the specific embodiment other than limited by the attached claims.

What is claimed is:

1. An endoscopic image filing system comprising an endoscope apparatus for inserting an endoscope having peculiar information into a coelom, for picking up an image of a region to be observed and for generating an endoscopic image, and an image filing apparatus for recording said endoscopic image, cleaning information from a cleaning apparatus for cleaning said endoscope, and said peculiar information.

2. An endoscopic image filing system according to claim 1, wherein said image filing apparatus reserves an endoscopic examination performed by said endoscope apparatus according to predetermined reservation information based on said cleaning information.

3. An endoscopic image filing system according to claim 2, wherein said image filing apparatus constructs reservation managing data as a database from said cleaning information and said reservation information.

4. An endoscopic image filing system according to claim 3, wherein said reservation managing data includes a cleaning flag for indicating whether said endoscope has been cleaned or not, and said image filing apparatus controls a status of said cleaning flag based on at least cleaning information.

5. An endoscopic image filing system according to claim 4, wherein said image filing apparatus controls a reservation of said endoscopic examination based on said status of said cleaning flag.

6. An endoscopic image filing system comprising an endoscope apparatus for inserting an endoscope having peculiar information into a coelom, for picking up an image of a region to be observed and for generating an endoscopic image;

an image filing apparatus connected to a hospital LAN, forming a network within a hospital, for recording said endoscopic image along with said peculiar information;

a cleaning apparatus which has recording means and is connected to said hospital LAN, for cleaning said endoscope; and a server connected to said hospital LAN, for controlling said hospital LAN, wherein
said cleaning apparatus includes:
a cleaning section for cleaning said endoscope,
cleaning control means for controlling a cleaning step of said cleaning section,
cleaning communication data generating means for generating cleaning communication data derived from cleaning information of said cleaning control means and said peculiar information, and
first data transmitting means for transmitting said cleaning communication data to said image filing apparatus; and
said image filing apparatus includes:
cleaning management data generating and updating means for generating and updating cleaning management data based on said cleaning communication data which is received, and
second data transmitting means for transmitting said cleaning management data to said server in order to record said cleaning management data on said recording means.

7. An endoscopic image filing system comprising an endoscope apparatus for inserting an endoscope having peculiar information into a coelom, for picking up an image of a region to be observed and for generating an endoscopic image;

an image filing apparatus for recording said endoscopic image and said peculiar information; and a cleaning apparatus for cleaning said endoscope, wherein said cleaning apparatus includes:
a cleaning section for cleaning said endoscope,
cleaning control means for controlling a cleaning step of said cleaning section,
cleaning communication data generating means for generating cleaning communication data derived from cleaning information of said cleaning control means and said peculiar information, and
data transmitting means for transmitting said cleaning communication data to said image filing apparatus, and
said image filing apparatus includes:
cleaning management data recording and controlling means for generating and updating cleaning management data based on said cleaning communication data which is received.

8. An endoscopic image filing system according to claim 7 wherein
said image filing apparatus reserves an endoscopic examination performed by said endoscope apparatus according to predetermined reservation information based on said cleaning management data.

9. An endoscopic image filing system according to claim 8 wherein
said image filing apparatus constructs reservation managing data as a database from said cleaning management data and said reservation information.

10. An endoscopic image filing system according to claim 9 wherein
said reservation managing data includes a cleaning flag for indicating whether said endoscope is cleaned or not, and
said image filing apparatus controls a status of said cleaning flag based on at least said cleaning management data.

11. An endoscopic image filing system according to claim 10 wherein
said image filing apparatus controls a reservation of said endoscopic examination based on said status of said cleaning flag.

12. An endoscopic image filing system comprising an endoscope apparatus for inserting an endoscope having peculiar information into a coelom, for picking up an image of a region to be observed and for generating an endoscopic image, and an image filing apparatus for recording said endoscopic image, cleaning information from a cleaning apparatus for cleaning said endoscope, and said peculiar information;

wherein said image filing apparatus reserves an endoscopic examination performed by said endoscope apparatus according to predetermined reservation information based on said cleaning information.

13. An endoscopic image filing system according to claim 12, wherein said image filing apparatus constructs reservation managing data as a database from said cleaning information and said reservation information.

14. An endoscopic image filing system according to claim 12, wherein said reservation managing data includes a cleaning flag for indicating whether said endoscope has been cleaned or not, and said image filing apparatus controls a status of said cleaning flag based on at least cleaning information.

15. An endoscopic image filing system according to claim 12, wherein said image filing apparatus controls a reservation of said endoscopic examination based on said status of said cleaning flag.

16. An endoscopic image filing system comprising an endoscope apparatus for inserting an endoscope having peculiar information into a coelom, for picking up an image of a region to be observed and for generating an endoscopic image, and an image filing apparatus for recording said endoscopic image, cleaning information from a cleaning apparatus for cleaning said endoscope, and said peculiar information, wherein said endoscope cleaning apparatus is separate from said endoscope.

* * * * *